United States Patent [19]

Ellis

[11] Patent Number: 5,258,921
[45] Date of Patent: Nov. 2, 1993

[54] AUTOMATED PURGE CONTROL OF STERILIZERS

[75] Inventor: Charles E. Ellis, Phelps, N.Y.

[73] Assignee: MDT Corporation, Torrance, Calif.

[21] Appl. No.: 648,568

[22] Filed: Jan. 31, 1991

[51] Int. Cl.$^5$ .......................... G06F 15/20; A61L 2/24
[52] U.S. Cl. ................................... 364/500; 364/570; 422/2; 422/111
[58] Field of Search ............... 364/483, 492, 477, 570, 364/500, 501, 503; 340/825.06; 422/2, 111133114

[56] References Cited

U.S. PATENT DOCUMENTS

| | | | |
|---|---|---|---|
| 4,298,955 | 11/1981 | Munday et al. | 364/500 X |
| 4,337,223 | 6/1982 | Kaye | 422/112 |
| 4,601,885 | 7/1986 | McClure | 422/114 |
| 4,680,706 | 7/1987 | Bray | 364/483 X |
| 4,845,594 | 7/1989 | Wilkerson | 364/483 X |
| 4,908,188 | 3/1990 | Jefferis, III et al. | 422/111 |
| 4,937,046 | 6/1990 | Anderson et al. | 422/33 X |
| 4,975,865 | 12/1990 | Carrette et al. | 364/500 X |
| 4,987,363 | 1/1991 | Gibbs et al. | 364/483 X |
| 5,019,996 | 5/1991 | Lee | 364/483 |
| 5,155,693 | 10/1992 | Altmayer et al. | 364/500 X |

Primary Examiner—Kevin J. Teska
Attorney, Agent, or Firm—Trask, Britt & Rossa

[57] ABSTRACT

Apparatus for and method of enhancing the safety of a vapor sterilizer using a programmed EEPROM signal to show when sterilant is present in the sterilizer chamber. The EEPROM signal electrically controls a door lock on a sterilizer door to prevent injury to an operator and achieve reduced sterilization costs, particularly when power interruptions occur.

13 Claims, 1 Drawing Sheet

AUTOMATED PURGE CONTROL OF STERILIZERS

BACKGROUND

1. Field

The invention relates to automated control systems for steam sterilizers and chemical sterilizers. More particularly, the invention pertains to control systems for determining the status of a sterilizer following power failure and controlling the operation according to the determined status.

2. State of the Art

Sterilizers using steam and/or chemicals as the sterilant are operated through a series of sequential steps in each operation cycle. Execution of these steps is typically controlled by a microprocessor control board with appropriate manual setting of sterilizing conditions and start/stop override options.

In the event of an extended power failure where the memory backup circuits are invalid, i.e. memory is erased, the control board is configured to initiate a purge upon restoration of power. The purge must be completed before the door lock is activated to the "open" position to avoid possible injury to the operator. The purge ensures that no steam or chemical vapors are present in the chamber before re-starting the sterilization cycle or opening the door. In the past, a purge was always necessary because there was no positive indication of the absence or presence of water or chemical sterilant in the sterilizer chamber following an extended power loss. Reprocessing of the load in the sterilizer required the initiation of a purge step to safely remove sterilant (if any) from the chamber. Efficient and effective sterilization requires close control of the sterilant quantity introduced into the sterilizer chamber. The quantity must be held within narrow limits. Excessive dosages of sterilant typically lead to longer cycle times because of slower heatup, extended vent and purge operations, etc. In addition, power requirements are increased, wastage of sterilant occurs, and the sterilizing process itself may be jeopardized.

Thus, the prior art uses a default purge step to ensure that the sterilizer chamber is free of sterilant and ready for use. The method is costly in terms of the extra time, energy and sterilant which it consumes.

The need remains for a method to indicate the status of the sterilizer chamber with regard to the absence or presence of sterilant, and using the method to eliminate non-necessary purges and to initiate necessary purges. The indication method must be reliable under extended conditions of line power loss.

SUMMARY OF THE INVENTION

The invention comprises an improvement in operating a microprocessor-controlled sterilizer. The need for a power-on purge cycle is established in permanent memory and alternatively, erased when the purge is completed. Thus, when an interruption of line power occurs, a purge of the sterilizer chamber is conducted only when required in accordance with the information in memory.

The method uses a dedicated bit of memory in an electrically erasable programmable read-only memory chip (EEPROM) for indicating when sterilant (water, steam, or chemical) is present in the sterilizer chamber. Whenever sterilant is introduced into the chamber, the controller software sets the EEPROM address to a specified value i.e. zero or 1.0, which represents a "sterilant present" signal. At the end of the timed purge phase of the cycle, after sterilant vapors have been removed from the chamber, the specified "sterilant present" value of the EEPROM address is changed to the alternate "sterilant absent" value.

The EEPROM data is read by the controller software each time power is applied to the sterilizer, i.e. power initialization.

Power interruption is sometimes brief. The sterilizer controller may be programmed to resume execution of the sterilization cycle at the point of power failure, provided all input data from the incomplete cycle remains intact in memory. The EEPROM is read by the controller software to confirm whether sterilant is present in the chamber.

When power loss occurs over an extended time period, such that a backup power supply is exhausted, a memory loss will occur, and the sterilization cycle must be restarted from the beginning of the cycle. In some cases, the materials to be sterilized are replaced by new materials, requiring personnel to open the sterilizer chamber. In other cases, it is desirable to inspect the sterilizer contents before continuing. This invention provides an indication of whether the chamber contains sterilant which needs to be purged before opening the chamber door. The EEPROM signal is used to automatically initiate a purge phase, or alternatively, unlock the door to permit the door to be opened without purging. Unnecessary purging of the chamber is eliminated while, at the same time, necessary purging is ensured.

BRIEF DESCRIPTION OF THE DRAWINGS

In the drawing, which illustrates what is currently regarded as the best mode for carrying out the invention.

DESCRIPTION OF THE ILLUSTRATED EMBODIMENT

Figure 1:
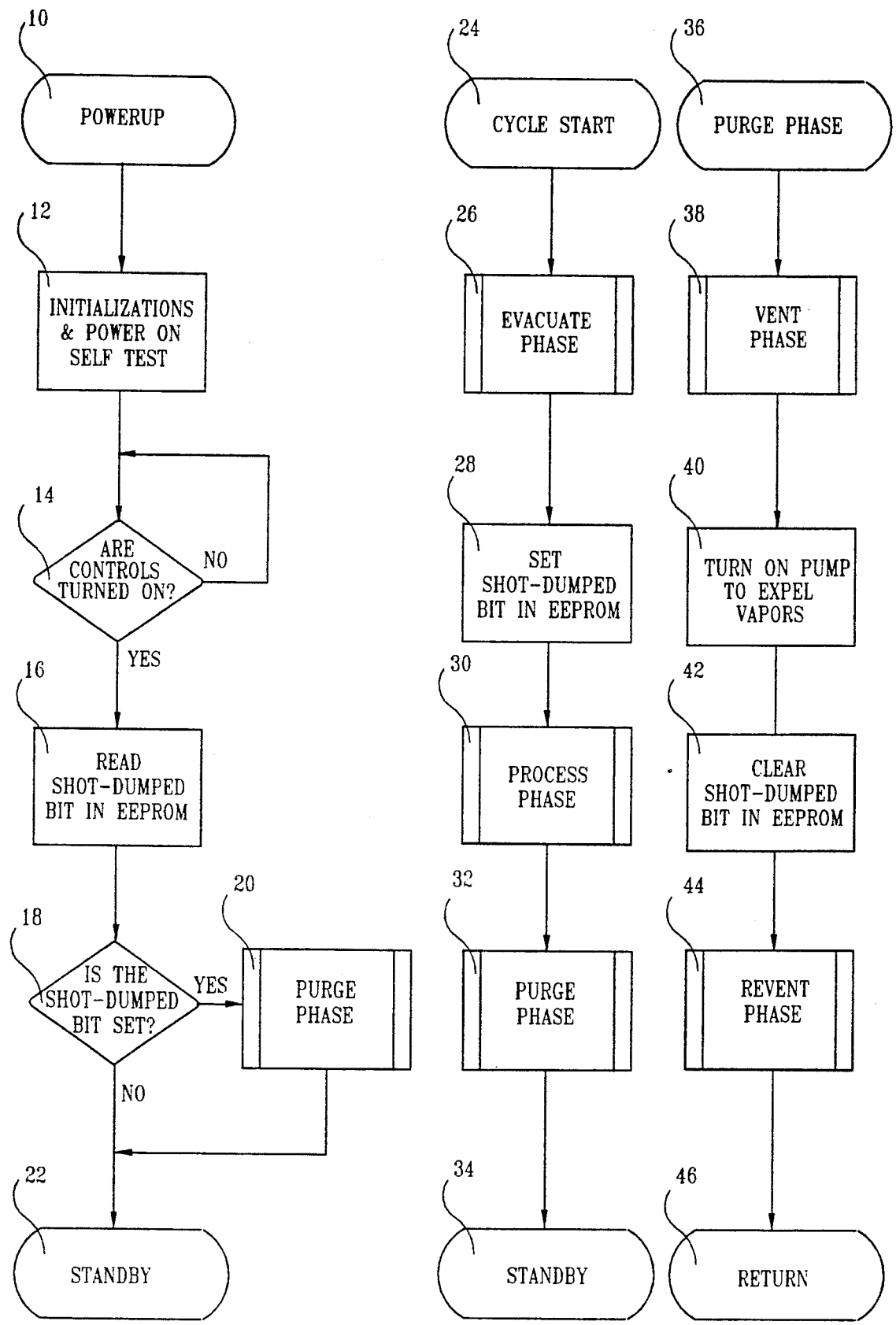
FIG. 1 is a flow chart of the powerup purge determination method of the invention.

The invention is an improvement in the microprocessor control of a sterilizer using steam and/or a chemical vapor or gas as the sterilant. FIG. 1 is a flow chart of portions of the computerized control program for a specific sterilizer. This sterilizer has a chamber with appropriate plumbing for introducing a liquid sterilant, for evacuation by a vacuum source, for purging with air or an inert gas, and for venting. The chamber door is typically locked by the microprocessor controller to prevent opening under possibly unsafe conditions or while processing is underway.

A "shot" of sterilant liquid is "dumped" into the chamber at a predetermined time in the sterilization cycle. The liquid is heated and vaporized by a heater(s) in the chamber to produce the desired sterilizing conditions. After processing of the goods at the sterilizing conditions, the vapor is purged from the chamber and the chamber cooled down so that the chamber door may be opened and the sterile goods removed.

The total sterilizer cycle has the following sequential phases controlled by a microprocessor:
 READY
 EVACUATE
 PROCESS
 PURGE, and
 COMPLETE In the READY phase, the unit is turned on and the particular sterilizing conditions (time, temperature, sterilant) are selected. The chamber door is opened and the unit loaded with goods to be sterilized. The door is closed and locked. Preheating of the chamber is also performed during this phase.

Following the READY phase, air in the chamber is partially evacuated by a vacuum pump in an EVACUATE phase.

Upon completion of the EVACUATE phase, a "shot" or dose of the sterilant in its liquid form, e.g., water to generate steam or liquid chemical such as formaldehyde, is "dumped" into the partially evacuated chamber. The liquid sterilant is heated and vaporized to steam or chemical vapor. The desired sterilization temperature and pressure are maintained for a specific sterilization time. This PROCESS phase is then followed by a PURGE phase.

In the PURGE phase, the vapor in the chamber is vented under the elevated chamber pressure. In addition, air or inert gas is introduced to purge the steam and/or chemical sterilant vapors from the chamber, and cool the chamber. Typically, a second venting or REVENT step completes the PURGE phase, leaving the chamber free of sterilant vapor, partially cooled, and at a slight overpressure.

Following the "PURGE" phase, the door may be opened and the sterilized goods removed from the chamber in a COMPLETE phase. When the door is opened, the heaters are reactivated to preheat the chamber for the next cycle. Alternatively, the sterilizer may be completely turned off.

The microprocessor controller of the sterilizer system normally has PROM, or programmable read only memory. The latter is used for the storage and use of operating instructions and related information in a fixed or "hardwired" form. The binary coded programs which control the sterilizer operations are permanently programmed into the PROM.

The operating conditions and data peculiar to a given cycle are entered into random access memory (RAM), which retains it only as long as power is supplied to the memory or until deliberately erased at cycle completion, etc. If the sterilizer unit has a battery backup unit, the input stored in RAM may be held valid for a period even when the main power supply is interrupted. However, backup units have limited available power, and typically a power interruption longer than about an hour results in RAM memory loss.

The invention includes electrically erasable programmable read-only memory (EEPROM) on a chip or other device.

The EEPROM chip, well known in the electronic memory storage art, has a software-activated electrical switch to permit erasure and rewriting of the contents of any given address. Thus, the contents are normally in a read-only mode which is permanent, i.e. unaffected by power interruption, but activation of the electrical switch permits access to the particular dedicated bit address for changing the content thereof.

The EEPROM bit stores data in a binary mode, i.e. alternatively as normally assigned values of "0" (zero) and "1" (one).

In this invention, an addressable bit is dedicated to storage of alternate binary values corresponding to "sterilant in chamber" and "sterilant not in chamber." The first value is inserted into the bit at the time when sterilant is first introduced into the chamber. The second value is inserted into the dedicated bit whenever a purge phase has been completed, ensuring that sterilant vapors have been removed from the sterilizer chamber. The purge phase may include one or more steps of venting the vapors or gas, using the pressure within the sterilizer, and one or more steps of introducing an inert gas, e.g. air or nitrogen into the chamber to sweep out the sterilant vapor or gases to a vapor collection means appropriate for safely disposing of the vapors.

As shown in FIG. 1, initiation of the power up step 10, typically by activating an electrical switch, automatically sets in motion several steps. First, initialization 12 of several functions and a power-on self test of the control circuitry is completed. If controls are not turned on, the software awaits their activation through decision block 14.

The software then reads in box 16 the dedicated "shot-dumped" bit in the EEPROM. If the bit is set to the first value, indicating that the chamber contains sterilant, decision block 18 initiates a purge phase 20 which removes sterilant from the chamber. The controls are then placed in a standby position 22 wherein typically the chamber door is opened, articles to be sterilized are placed in the chamber, and the chamber door shut.

The purge phase 20 is bypassed following powerup 10 if the dedicated bit in EEPROM contains the second value, indicating that the chamber has been purged of sterilant. The controller goes to the "standby" position 22.

The remainder of the sequential phases as generally controlled by the microprocessor controller are shown in the second set of steps starting with cycle start initialization 24. The figure shows the first action to be an evacuate phase 26 in which air in the sterilizer chamber is partially evacuated by a vacuum pump. Evacuate phase 26, and the other phases shown, typically involve several discrete operating steps.

Following the evacuate phase 26, and just prior to introducing the sterilant, the EEPROM addressable bit is addressed to create a first binary value therein. The value may be either the zero value or the alternate $+1$ value. The value inserted represents the "sterilant in chamber" condition of the sterilizer. In the example of FIG. 1, the sterilant is introduced into the chamber by a "shot-dump" method 28, and the bit is termed a "shot-dumped bit."

The process phase 30 then completes the sterilization of the articles, including vaporization of the sterilant if it is introduced as a liquid, and maintenance of the desired temperature and pressure conditions for the desired sterilization period.

A purge phase 32 is then conducted to remove the sterilant from the sterilizer chamber, and the sterilizer control is placed on standby 34, awaiting removal of the sterilized articles and powerup/initialization of another sterilization cycle.

Purge cycles 20 and 32 may be identical, or they may be slightly different in the particular steps. For example, cycle 20 may include a preheating to ensure that all liquid sterilant is vaporized for purging from the sterilizer chamber.

As shown in the figure, purge phase start 36 initiates steps corresponding to purge phase 20 and/or 32. A vent phase 38 may comprise several discrete steps to discharge the sterilant under the chamber pressure. A pump (or other source of air or gas) is turned on in step 40 to purge vapors from the chamber. The dedicated bit in EEPROM is then addressed in step 42 to erase the "shot-dumped" value which was previously inserted therein. A re-vent phase 44 is then conducted to reduce the chamber pressure and remove the final traces of vapor sterilant. The control is then directed in step 46 to return to standby 22, if the conducted purge phase was phase 20, or to standby 34 if the conducted purge phase was phase 32.

Alternatively, the presence or absence of sterilant in the chamber is displayed for the operator, and the purge phase is initiated manually by the operator.

In one aspect of the invention, the chamber has an electrically lockable door which activates the lock to a "locked" position when the EEPROM bit has the first value, and to an "unlocked" position when the EEPROM bit has the second or alternate value corresponding to no sterilant in the chamber. Thus, unsafe opening of the door by an operator is prevented, to avoid contact with the hot sterilant vapor. In addition, operating the sterilizer with a double dose of sterilant is avoided, as is the unnecessary purging of an empty chamber.

The EEPROM maintains the data inserted in the programmable bit when extended power interruptions occur, thus providing a definite indication of whether the chamber requires purging. Furthermore, opening of the chamber is prevented until it is purged of sterilant.

Thus, the invention may be used to provide an indication of whether the chamber contains or does not contain sterilant. Preferably, this information is used by a microprocessor in automatic control of the sterilization process.

Reference herein to details of the illustrated embodiments is not intended to restrict the scope of the appended claims which themselves recite those features regarded as important to the invention.

What is claimed is:

1. An improvement in a sterilizer having chamber means with an access door for placement and removal of goods, an electrically controllable lock on said door for maintaining said door in a sealably closed position, dump means for introducing a sterilant into said chamber for sterilizing said goods placed therein, purge means for purging said chamber with a gas, and digital computerized controller means having program means for controlling said dump means, purge means and lock means in a sequence of discrete operating steps comprising a sterilization cycle; said improvement comprising:
    a first signal generated upon activation of said dump means;
    a second signal generated upon completion of the operation of said purge means;
    EEPROM storage means for entry and subsequent electrical erasure of binary values in an addressable bit in said EEPROM by said first and second signals addressed thereto, wherein one of said signals enters a first binary value in said bit and the other of said signals enters an alternate binary value; and
    EEPROM reading means for determining said binary value and locking and maintaining said lock in a locked position when said binary value corresponds to said first signal and opening said lock to an unlocked position when said binary value corresponds to said second signal.

2. The improvement of claim 1, wherein said sterilant introduced into said chamber means is a liquid and said purge means includes means to heat said chamber means to evaporate said liquid to a vapor for purging from said chamber means.

3. The improvement of claim 1, wherein one of said first and alternate said binary values is a positive value entered by said first signal in said addressable bit and the other said value comprises erasure of said entered value.

4. The improvement of claim 1, wherein said EEPROM reading means reads said addressable bit upon power initialization of said controller means.

5. The improvement of claim 4, wherein said power initialization of said controller means is responsive to completion of said sterilization cycle and resumption of power following unplanned power interruption.

6. The improvement of claim 4, wherein said controller means initiates operation of said purge means when said binary value reading at said power initialization corresponds to said first signal.

7. An apparatus for selectively purging a vessel of vapors, comprising:
    first sensing means for sensing introduction of process vapors into said vessel, and activated by said introduction of said vapors;
    EEPROM storage means having an addressable bit for storage of alternative binary values therein;
    first signal generating means for communicating a first signal to said addressable bit to create a first binary value therein, said first signal corresponding to said activation of said first sensing means;
    second sensing means for sensing purging of said process vapors from said vessel, said second sensing means activated by completion of said purging;
    second signal generating means for communicating a second signal to said addressable bit to create an alternative binary value therein, said second signal corresponding to said activation of said second sensing means; and
    reading means to read said addressable bit and indicate one of said first and alternative binary values therein corresponding to said presence and absence, respectively, of said vapors in said vessel.

8. An improvement in a method for sterilizing articles by a sterilant vapor in an electrically power operated sterilizer having a sterilizer chamber with an electrically operated door lock for a lockable door, said method including:
    turning on power to the sterilizer;
    unlocking and opening the lockable door and loading said sterilizer with said articles;
    closing and locking said door;
    introducing sterilant to said sterilizer chamber and contacting said articles with vapors of said sterilant for a sterilization period to sterilize said articles;
    venting said chamber to vapor collection means to remove a portion of said sterilant vapors therefrom;
    introducing an inert gas into said chamber to purge remaining said sterilant vapors therefrom; and
    opening said chamber and removing said articles therefrom; wherein the improvement comprises:
    addressing an EEPROM addressable bit upon introduction of said sterilant to said chamber to create a first binary value in said EEPROM bit;
    addressing said EEPROM addressable bit upon completion of said purge step to create an alternate binary value in said EEPROM bit;
    reading said EEPROM addressable bit upon said turning on of said power; and alternatively initiating said steps of venting, purging and removing said articles if said read EEPROM bit contains said first binary value, and continuing to said unlocking and opening of said door if said read EEPROM bit contains said alternate binary value.

9. The improvement of claim 8, further including actuating the door lock to a locked position when said EEPROM addressable bit contains said first binary value, and to an unlocked position when said EEPROM addressable bit contains said alternate binary value.

10. The improvement of claim 8, wherein said first binary value and said alternate binary value comprise a positive value and the erasure thereof, respectively.

11. An improvement in a method for sterilizing articles in an electrically power operated sterilizer by a sterilant vapor introduced into a sterilizing chamber as a liquid and vaporized therein, said chamber having an electrically operated door lock for a lockable door and said method including:

turning on electrical power to the sterilizer;
 opening said lockable door and placing said articles in said chamber;
 closing and locking said door;
 introducing said sterilant as a vaporizable liquid into said chamber;
 vaporizing said sterilant with a heater to produce a sterilizing vapor at elevated temperature and pressure;
 maintaining said elevated temperature and pressure for a sterilization period to sterilize said articles;
 venting said chamber to vapor collection means to remove a portion of said sterilant vapors therefrom;
 introducing an inert gas into said chamber to purge remaining said sterilant vapors therefrom; and
 opening said chamber and removing said articles therefrom; wherein the improvement comprises:
  addressing an EEPROM addressable bit just prior to introducing said sterilant to said chamber to create a first binary value in said EEPROM bit to replace any other binary value in said addressable bit,
  addressing said EEPROM addressable bit upon completion of said purge step to create an alternate binary value in said EEPROM bit to replace any other binary value in said addressable bit,
  reading said EEPROM addressable bit upon said turning on of said electrical power,
  initiating a step of heating said chamber followed by said steps of venting, purging, opening, and removing said articles from said chamber if said read EEPROM addressable bit contains said first binary value, and
  alternatively unlocking and opening said door and removing said articles from said chamber if said read EEPROM bit contains aid alternate binary value.

12. The improvement of claim 11, further including actuating the door lock to a locked position when said EEPROM addressable bit contains said first binary value, and to an unlocked position when said EEPROM addressable bit contains said alternate binary value.

13. The improvement of claim 11, wherein said first binary value and said alternate binary value comprise a positive value and the erasure thereof, respectively.

* * * * *